United States Patent
Deegan

(10) Patent No.: US 8,708,888 B2
(45) Date of Patent: *Apr. 29, 2014

(54) BODY IMPLANTABLE FABRIC HAVING CLOSED LOOP KNIT

(75) Inventor: Christopher Deegan, North St. Paul, MN (US)

(73) Assignee: Coloplast A/S, Humlebaek (DK)

(*) Notice: Subject to any disclaimer, the term of this patent is extended or adjusted under 35 U.S.C. 154(b) by 134 days.

This patent is subject to a terminal disclaimer.

(21) Appl. No.: 13/019,395

(22) Filed: Feb. 2, 2011

(65) Prior Publication Data

US 2011/0190573 A1    Aug. 4, 2011

Related U.S. Application Data

(63) Continuation of application No. 12/699,882, filed on Mar. 2, 2010.

(30) Foreign Application Priority Data

Feb. 3, 2010  (DK) .................................. 2010 70036

(51) Int. Cl.
*A61F 2/00* (2006.01)
*A61F 2/02* (2006.01)
*D04B 1/06* (2006.01)

(52) U.S. Cl.
USPC .............................. 600/37; 600/30; 66/169 A

(58) Field of Classification Search
USPC ..................... 600/30, 37; 66/169 A
See application file for complete search history.

(56) References Cited

U.S. PATENT DOCUMENTS

| | | | |
|---|---|---|---|
| 2,038,493 A * | 4/1936 | Jones | 66/169 R |
| 2,452,835 A | 11/1948 | Cobert | |
| 4,769,038 A | 9/1988 | Bendavid et al. | |
| 5,292,328 A * | 3/1994 | Hain et al. | 606/151 |
| 6,953,428 B2 | 10/2005 | Gellman et al. | |
| 6,971,252 B2 | 12/2005 | Therin et al. | |
| 7,594,921 B2 | 9/2009 | Browning | |
| 2004/0172048 A1 | 9/2004 | Browning | |
| 2004/0249397 A1 | 12/2004 | Delorme et al. | |
| 2004/0249473 A1 | 12/2004 | Delorme et al. | |
| 2005/0234291 A1 | 10/2005 | Gingras | |
| 2006/0101863 A1 * | 5/2006 | Oya et al. | 66/202 |

(Continued)

FOREIGN PATENT DOCUMENTS

| | | | |
|---|---|---|---|
| EP | 1520552 A1 | 4/2005 | |
| GB | 363383 | * 12/1931 | |

(Continued)

OTHER PUBLICATIONS

Mentor, Sep. 2005: ARIS Trans-Obturator Tape.

(Continued)

*Primary Examiner* — Charles A Marmor, II
*Assistant Examiner* — Kaylee Wilson
(74) *Attorney, Agent, or Firm* — Coloplast Corp.; Nick Baumann

(57) ABSTRACT

A body implantable fabric includes an organ support device separated from a knit material and has a filament forming a chain of loops that extend along a length of the knit material. The chain of loops are coupled together by having each loop suspended by a neighboring loop, and at least one loop in the chain of loops having the filament tied around that one loop to form a closed loop.

12 Claims, 9 Drawing Sheets

(56) References Cited

U.S. PATENT DOCUMENTS

| | | |
|---|---|---|
| 2006/0229493 A1* | 10/2006 | Weiser et al. ............ 600/37 |
| 2006/0281967 A1 | 12/2006 | Meneghin |
| 2007/0032881 A1 | 2/2007 | Browning |
| 2007/0049791 A1 | 3/2007 | Merade et al. |
| 2008/0177132 A1 | 7/2008 | Alinsod et al. |
| 2009/0326565 A1 | 12/2009 | Trabucco |

FOREIGN PATENT DOCUMENTS

| | | |
|---|---|---|
| GB | 363383 A | 12/1931 |
| WO | 2005027786 A1 | 3/2005 |
| WO | 2005110243 A2 | 11/2005 |
| WO | 2007/097994 | 8/2007 |
| WO | 2008048971 | 4/2008 |
| WO | 2008048971 A1 | 4/2008 |
| WO | WO 2008048971 A2 * | 4/2008 ............ A61B 5/00 |
| WO | 2008/057269 | 5/2008 |
| WO | 2008058163 A2 | 5/2008 |

OTHER PUBLICATIONS

Office Action mailed on Aug. 31, 2012 in U.S. Appl. No. 12/699,882.

* cited by examiner

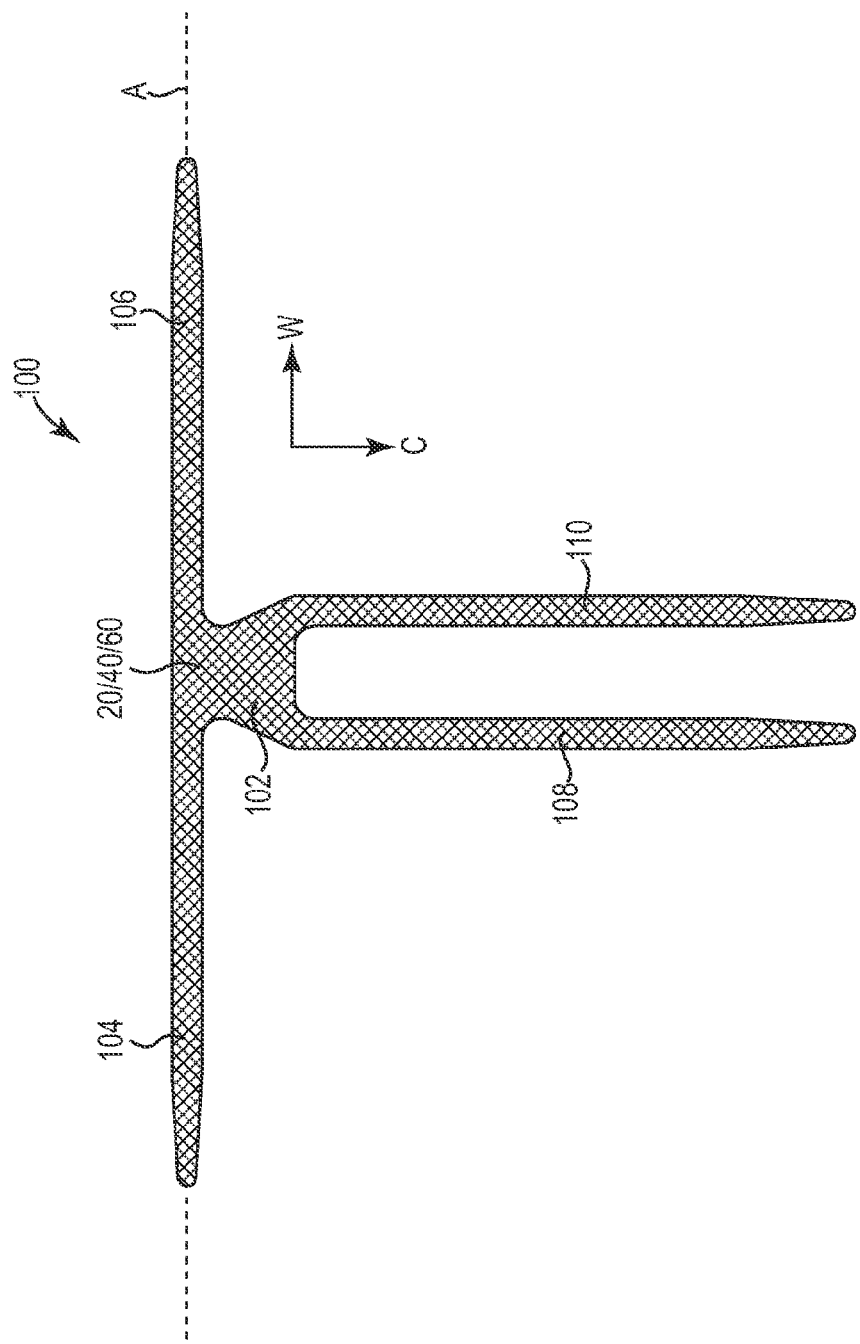

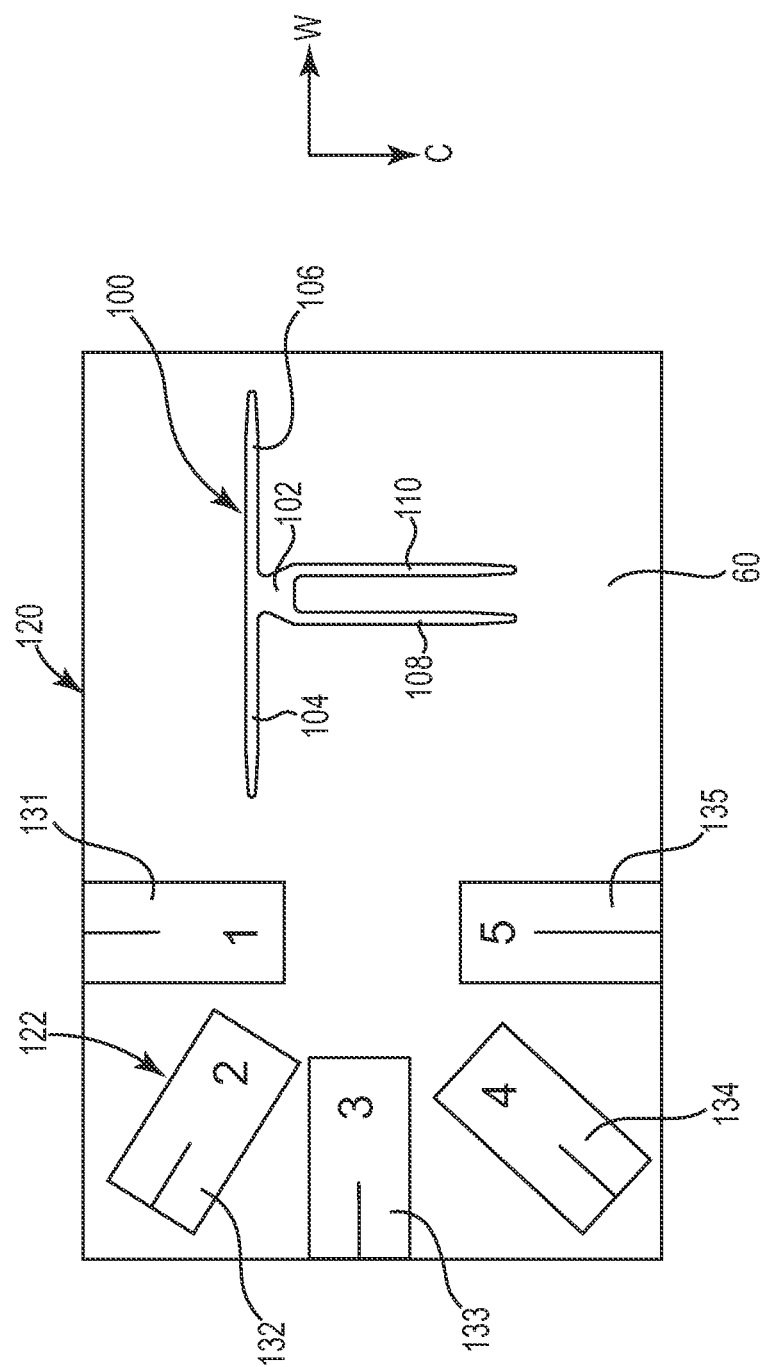

BODY IMPLANTABLE FABRIC HAVING CLOSED LOOP KNIT

BACKGROUND

Incontinence in men relates to a reduction or loss in urethral sphincter function. For example, the prostatic urethra is at times removed or altered during prostate surgery, which can lead to a reduced ability in the urethra to coaptate. Incontinence in women relates to a loss in support of the female urethra, for example as one or more of the pelvic organs prolapse, which allows urine to leak out of the urethra. Pelvic organ prolapse is a disorder related to the dropping down (prolapse) of the bladder, rectum, or uterus caused by weakness or injury to ligaments, connective tissue, or muscles of the pelvis.

A hernia is a protrusion of a body organ through the wall of the body cavity.

Meshes are at times implanted into the body to support the urethra, or to support prolapsed organs, or to reinforce the wall of the body cavity. Meshes include knit meshes and woven meshes.

FIG. 1 is a top view of a prior art knit mesh 10 including a filament 12 knit on a path to form a chain of loops 14, where each loop 16 in the chain of loops 14 is suspended by a neighboring loop 18. In this manner, the loops 14 are secured as they are knit by passing a newly formed loop (e.g., loop 16) through a previously formed loop (e.g., loop 18). The chain of loops that run left-to-right in FIG. 1 are referred to as a wale W. The path that the filament 12 follows is referred to as a course C. The loops 14, 16, 18 of the prior art knit mesh 10 will unravel if pulled with a sufficient force, or if one of the loops is broken or severed.

A woven mesh is not a knit mesh. A woven mesh is formed by threads that run parallel in a lengthwise direction (warp threads) and cross with a separate set of parallel threads placed in a crosswise direction (weft threads). The meandering course C that forms the loops 14, 16, 18 of the prior art knit mesh 10 provide the knit mesh 10 with greater elasticity (e.g., stretchiness) over the woven mesh since the loops move within each other. Some surgeons prefer knit mesh materials over woven mesh materials for body implantation around the generally curved body organs.

Knitted mesh materials are effective for use as body implantable fabrics. However, these knit mesh materials are susceptible to unraveling or tearing when pulled on during placement in the body, which can lead to undesirable tearing of the knit mesh.

SUMMARY

One aspect provides a body implantable fabric including an organ support device separated from a knit material and having a filament forming a chain of loops that extend along a length of the knit material. The chain of loops are coupled together by having each loop suspended by a neighboring loop, and at least one loop in the chain of loops having the filament tied around that one loop to form a closed loop.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

FIG. 5 is a top view of one embodiment of a body implantable device made from a closed loop knit mesh.

FIG. 6 is a schematic view of a sheet of closed loop knit mesh including a layout of the body implantable device illustrated in FIG. 5 and a layout of a collection of coupons oriented in various directions on the sheet.

DETAILED DESCRIPTION

Figure 1:
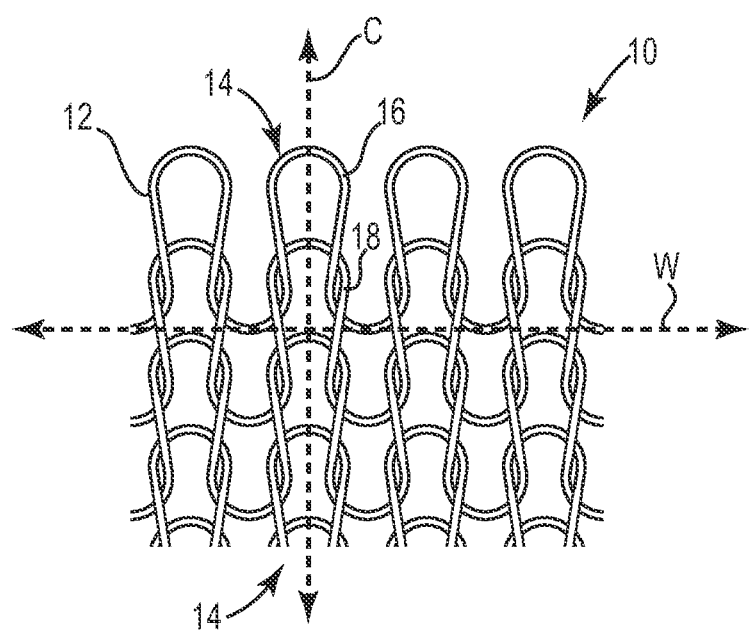
FIG. 1 is a top view of a prior art knit mesh.

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

It is to be understood that the features of the various exemplary embodiments described herein may be combined with each other, unless specifically noted otherwise.

Tissue includes soft tissue, which includes dermal tissue, sub-dermal tissue, ligaments, tendons, or membranes. As employed in this specification, the term "tissue" does not include bone.

Some medical procedures directed to addressing incontinence in men or to pelvic floor repair in women include placing a knit mesh inside of the body and pulling on the mesh to provide a desired level of tension of the mesh relative to the body organ that is being supported.

Some knitted meshes are "knit-to-width" on a machine that makes the desired support device at a specific width. These knit-to-width supports have some reinforcing structure along the perimeter, such as additional stitches, that is applied to the edges of the knit-to-width support to give the support improved strength and reduce or eliminate stray or loose ends. The knit-to-width support devices are potentially expensive to manufacture and are generally rectangular in shape since such machines lack the capability to knit complex shapes.

In contrast, embodiments provide a sheet of knit mesh having closed loops from which a support device is cut out or removed. The shed of knit mesh closed loops is suitable for body implantation and has at least one loop in a chain of knitted loops that includes a filament tied around one of the loops to form a closed loop. The shape of the devices that may be removed from the sheet of knit mesh closed loops is essentially unlimited and the unit cost is substantially lower than knit-to-width supports. In addition, the device removed or cut out from the sheet of knit mesh closed loops may have frayed or severed ends, but these ends do not unravel the knit since the knit material includes at least one, and like several, closed loops.

The sheet of knit mesh closed loops provides the support devices with good stretch/elasticity (about 200% at about 15 lbf) and tear resistance of at least 5 pounds force (lbf) in both the machine and the cross direction. Support devices removed from the sheet of knit mesh closed loops have improved tear resistance over devices removed from sheets of knit loops, which allows the surgeon to pull on arms of the support device to apply tension or pressure to the organs that are being supported without tearing the arms.

Figure 2A:
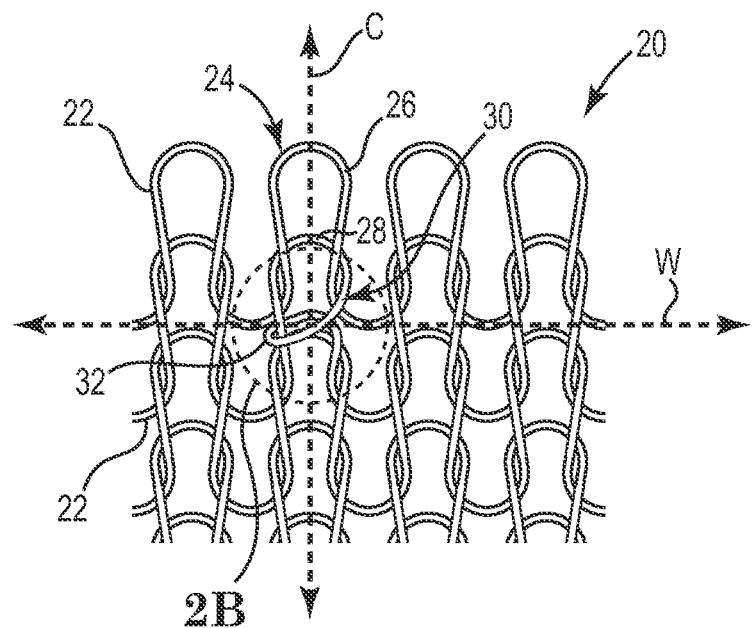
FIG. 2A is a top view of one embodiment of a closed loop knit mesh.

FIG. 2A is a top view of one embodiment of a closed loop knit mesh 20. The closed loop knit mesh 20 has a filament 22 forming a chain of loops 24 that extend along a length of the knit material to form a wale W, where the chain of loops 24 is coupled together by having each loop 26 suspended by a neighboring loop 28, and at least one loop 30 in the chain of loops 24 has the filament 22 tied around that one loop 30 to form a closed loop 32. The closed loop 32 is formed by the filament 22 that is placed to individually encircle or terminate the loop 30. In one embodiment, the closed loop knit mesh 20 is provided as a sheet of material from which a body implantable support is removed for use in a patient.

Figure 2B:
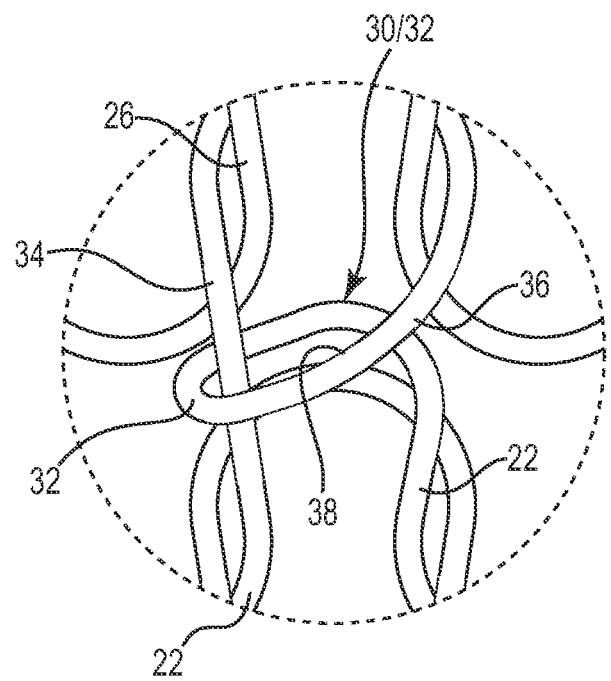
FIG. 2B is an expanded view of a closed loop of the closed loop knit mesh illustrated in FIG. 2A.

FIG. 2B is an expanded view of the closed loop 32. The filament follows a path that loops through the neighboring loop 26, and includes an ascending loop segment 34 coupled to a descending loop segment 36 by a transverse loop segment 38. The transverse loop segment 38 extends from the descending loop segment 36 and is tied around the ascending loop segment 34. The closed loop knit mesh 20 is illustrated as having one closed loop 32, although other closed loop knit meshes are described below having multiple closed loops.

It has been surprisingly discovered that the closed loop knit mesh 20 provides support devices that, when removed from the sheet of the closed loop knit mesh 20, have significantly improved tear resistance as compared to meshes that are knit without closed loop(s). For example, when an open loop knit mesh similar to the knit mesh 10 (FIG. 1) is compared to the closed loop knit mesh 20, where the meshes have a comparable basis weight of about 90-110 grams per square meter, the open loop knit mesh 10 will have a tear resistance of about 3 lbf in a direction across the wale W and the closed loop knit mesh 20 will have a tear resistance of about 7 lbf in a direction across the wale W. In other words, for similar basis weights, the closed loop knit mesh 20 provides over a 100% improvement in cross-wale tear resistance over the prior art open loop knit mesh 10.

Body implantable fabrics are suitably fabricated from meshes having a basis weight of between about 80-120 grams per square meter, and for these basis weights, the closed loop knit mesh 20 described above provides the body implantable fabric with a tear resistance of not less than 5 lbf in any direction (i.e., across the wale W or across the course C). In one embodiment, for the basis weights between 80-120 grams per square meter, the closed loop knit mesh 20 described herein provides body implantable devices fabricated from the closed loop knit mesh 20 with about a 100% improvement in tear resistance in its weakest direction as compared to open loop knit meshes illustrated in FIG. 1.

The filament 22 of the closed loop knit mesh 20 is a polymer filament or a natural fiber filament. In one embodiment, the filament 22 is a polypropylene filament having a diameter of about 0.0075 inches. Other suitable filaments include filaments fabricated from other polymers or natural materials, such as silk, cotton, or wool.

Figure 3A:
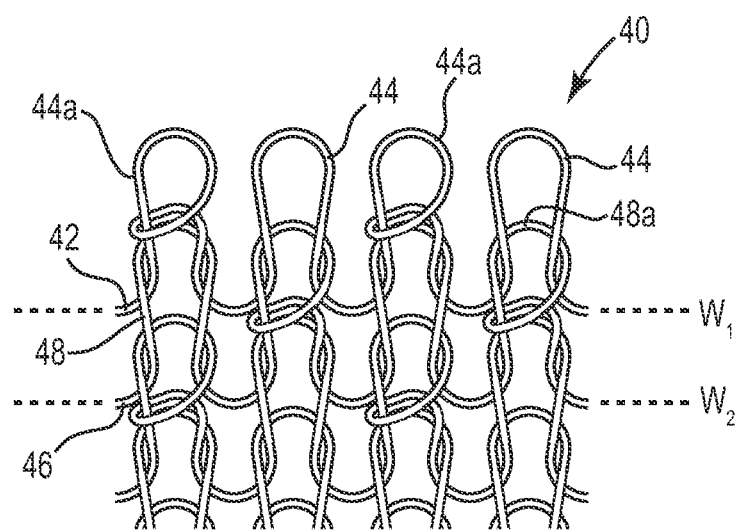
FIG. 3A is a top view of one embodiment of a knit mesh with half of the loops closed.

FIG. 3A is a top view of one embodiment of a knit mesh 40 having half of the loops closed. The knit mesh 40 includes a first filament 42 that forms a first chain of loops 44 along a first wale W1 and a second filament 46 that forms a second chain of loop 48 along a second wale W2. The first filament 42 is tied around individual alternating loops 44a in the first chain of loops 44 and the second filament 46 is tied around alternating loops 48a in the second chain of loops 48 to provide the knit mesh 40 with approximately half of the loops closed.

Figure 3B:
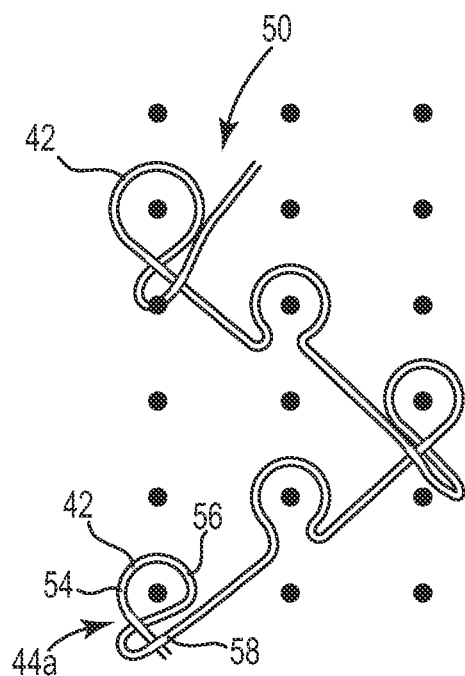
FIG. 3B is a schematic of one embodiment of a needle path employed for knitting the closed loop knit mesh illustrated in FIG. 3A.

FIG. 3B is a schematic of one embodiment of a needle path 50 employed for knitting the closed loop knit mesh 40 illustrated in FIG. 3A. The filament 42 is stitched along the path 50, where the path 50 guides the filament 42 along an ascending loop segment 54 and a descending loop segment 56 that culminates in a transverse loop segment 58 that is tied around the ascending segment 54 before moving on to the next loop in the stitch along the wale. It is to be understood that the black dots provided in the schematic view of FIG. 3B do not necessarily have a physical presence in real space but are provided to give a perspective to the path 50 that is followed by a needle that places the filament 42.

In general, the closed loop knit mesh 40 is fabricated on a machine using one or more needles. For example, a single needle could be employed to stitch a single filament 42 along repeated paths 50 to form a closed loop knit mesh 40. Alternatively, multiple needles attached to multiple bars of a knitting machine are moved along the path 50 to fabricate the closed loop knit mesh 40 from multiple stands of filaments.

Figure 4A:
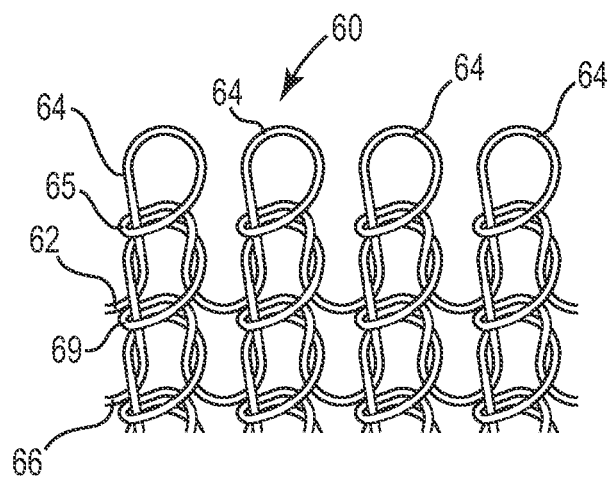
FIG. 4A is a top view of one embodiment of a knit mesh with substantially all of the loops closed.

FIG. 4A is a top view of one embodiment of a knit mesh 60 having all of the loops closed. The knit mesh 60 includes a first filament 62 that forms a first chain of loops 64 along a first wale W1 and a second filament 66 that forms a second chain of loop 68 along a second wale W2. The first filament 62 is tied around each individual loop 64 (for example at 65) and the second filament 66 is tied around each individual loop 68 (for example at 69) to provide the knit mesh 60 with approximately all of the loops closed.

Figure 4B:
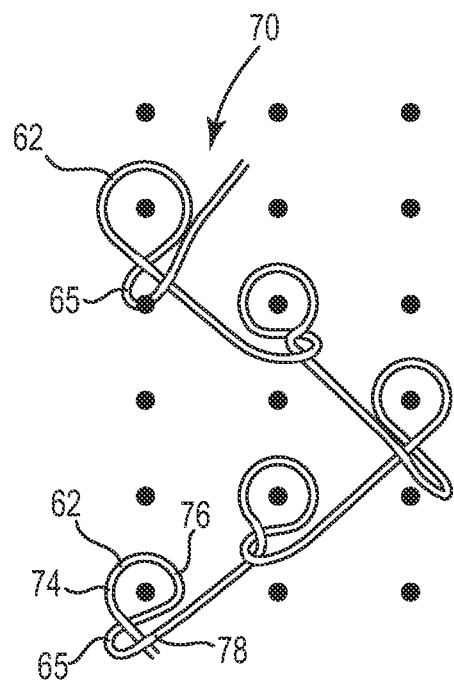
FIG. 4B is a schematic of one embodiment of a needle path employed for knitting the closed loop knit mesh illustrated in FIG. 4A.

FIG. 4B is a schematic of one embodiment of a needle path 70 employed for knitting the closed loop knit mesh 60 illustrated in FIG. 4A. The filament 62 is stitched along the path 70, where the path 70 guides the filament 62 along an ascending loop segment 74 and a descending loop segment 76 that culminates in a transverse loop segment 78 that is tied around the ascending loop segment 74 at 65 before moving on to the next loop in the stitch along the wale. Again, the black dots provided in the schematic view of FIG. 4B do not necessarily have a physical presence and the closed loop knit mesh 60 is suitably fabricated on a machine using one or more needles.

FIG. 5 is a top view of one embodiment of a body implantable support 100 as suitably fabricated from the closed loop knit meshes 20, 40, or 60. In one embodiment, the support 100 is a body implantable support device that is die-cut from one of the closed loop knit meshes 20, 40, or 60 and is employed to treat incontinence in a male patient.

In one embodiment, the support 100 includes a body 102 with a first pair of arms 104, 106 extending from the body 102 and a second pair of arms 108, 110 extending from the body 102. In one embodiment, each of the first pair of arms 104, 106 is disposed on a major axis A such that arm 104 is opposed to arm 106. In one embodiment, arm 108 is parallel to arm 110 and both extend from the body 102 substantially perpendicular to the major axis A. In one embodiment, the support 100 is fabricated as an incontinence treatment support and arms 104, 106 are provided as transobturator arms and arms 108, 110 are provided as pubic arms or suprapubic arms.

The support 100 is fabricated from one of the closed loop knit meshes 20, 40, or 60 and is so configured to have improved tear resistance over knit meshes that do not have a closed loop or multiple closed loops. In one embodiment, the direction of the wales W of the closed loop knit mesh 20, 40, 60 run along the trans obturator arms 104, 106 as illustrated in FIG. 5, and the suprapubic arms 108, 110 are oriented perpendicular to the axis A and are aligned with the courses C of the closed loop knit meshes 20, 40, or 60.

During implantation of the support 100, the trans obturator arms 104, 106 are placed in tension such that the body 102 elevates and compresses the tissue surrounding the male urethra. Trans obturator arms exhibit a tendency to tear in the direction perpendicular to the axis A (e.g., across the arm). The closed loop knit meshes 20, 40, or 60 provide the support 100, and in particular the trans obturator arms 104, 106, with improved cross-arm tear resistance of 5 lbf or more for a basis weight of between about 90-110 grains per, square meter, as described below.

FIG. 6 is a schematic view of a sheet 120 of the closed loop knit mesh 60 (FIG. 4A) including a layout for the removal of the support 100 and a layout for the removal of a collection of coupons 122 oriented in various directions on the sheet 120. The support 100 is removed from the sheet 120 of knit mesh material 60 by die cutting, laser cutting, or heat cutting. The coupons 122 are removed from the sheet 120 along the directions illustrated. For example, the coupon 131 is removed from the sheet 120 in the Direction 1 that is perpendicular to the axis A and perpendicular to the direction of the wales W (FIG. 5). The coupon 132 is removed from the sheet 120 in a Direction 2 that is about midway between Direction 1 and the Direction 3 along which the coupon 133 is oriented. The coupon 133 is aligned parallel with the wales W and perpendicular to the courses C (FIG. 5). The coupon 134 is oriented midway between the coupon 133 and the coupon 135, where the coupon 135 is oriented in the Direction 5, or 180 degrees out of phase from Direction 1 of the coupon 131.

Although FIG. 5 and FIG. 6 illustrate the arms 104, 106 aligned with the Wale W, it is to be understood that the orientation of the arms 104, 106 is not limited by the illustrated figures and the arms 104, 106 may be oriented in other directions.

COMPARATIVE EXAMPLES

Comparative Mesh 1 refers to the coupons 122 that were removed from the sheet 120 of the closed loop knit mesh 60 (at approximately one-half of the size as specified by ASTM D2261).

PA mesh refers to similar coupons remove from the prior art open loop knit mesh 10 (FIG. 1) along the Directions 1, 2, ... 5 illustrated in FIG. 6.

The Comparative Mesh 1 and the PA mesh were evaluated for tensile strength (Table 1) and tear resistance (Table 2) as listed below.

TABLE 1

Tensile Strength (lbf)

| Coupon Direction | PA mesh | Comparative Mesh 1 |
|---|---|---|
| Direction 1 (wales W) | 12.9 | 26.0 |
| Direction 2 (45°) | 22.0 | 20.8 |
| Direction 5 (Courses C) | 25.3 | 32.4 |

TABLE 2

Tear Resistance (lbf)

| Coupon Direction | PA mesh | Comparative Mesh 1 |
|---|---|---|
| Direction 1 (wales W) | 3.3 | 7.1 |
| Direction 2 | 4.5 | 11.4 |
| Direction 3 | 10.6 | 10.4 |
| Direction 4 | 11.5 | 11.6 |
| Direction 5 | 11.7 | 10.8 |

Table 3 below compares the physical properties of the prior art open loop knit mesh (PA mesh) to the closed loop mesh 60 (Comparative Mesh 1 with all of the loops closed) and the closed loop mesh 40 (Comparative Mesh 2 with half of the loops closed).

TABLE 3

Physical Properties

| Mesh | Thickness (mils) | Basis Weight (g/m$^2$) | Courses per inch | Pore size (mm$^2$) |
|---|---|---|---|---|
| PA mesh | 23.5 | 110 | 36 | 0.631 |
| Comparative Mesh 1 | 25.0 | 91.4 | 29 | 0.734 |
| Comparative Mesh 2 | 26.4 | 110 | 36 | 0.420 |

The body implantable support 100 fabricated from the closed loop mesh 60 has significantly improved tensile strength along the Direction 1 (e.g., along the wales W corresponding to the trans obturator arms 104, 106), and significantly improved tear resistance in the Direction 1 and the Direction 2, which allows a surgeon to pull on the trans obturator arms 104, 106 during implantation of the support 100 while minimizing the undesirable possibility of tearing the arms 104, 106.

The body implantable support 100 fabricated from the closed loop mesh 60 has provides the trans obturator arms 104, 106 with an elongation of about 270% at an elongation-to-break force of about 21 lbf, which is similar to meshes fabricated from open loop meshes that have an elongation of about 330% at an elongation-to-break force of about 25 lbf. That is to say, the body implantable support 100 fabricated from the closed loop mesh 60 has acceptable elongation properties along with improved tear resistance.

Figure 7:
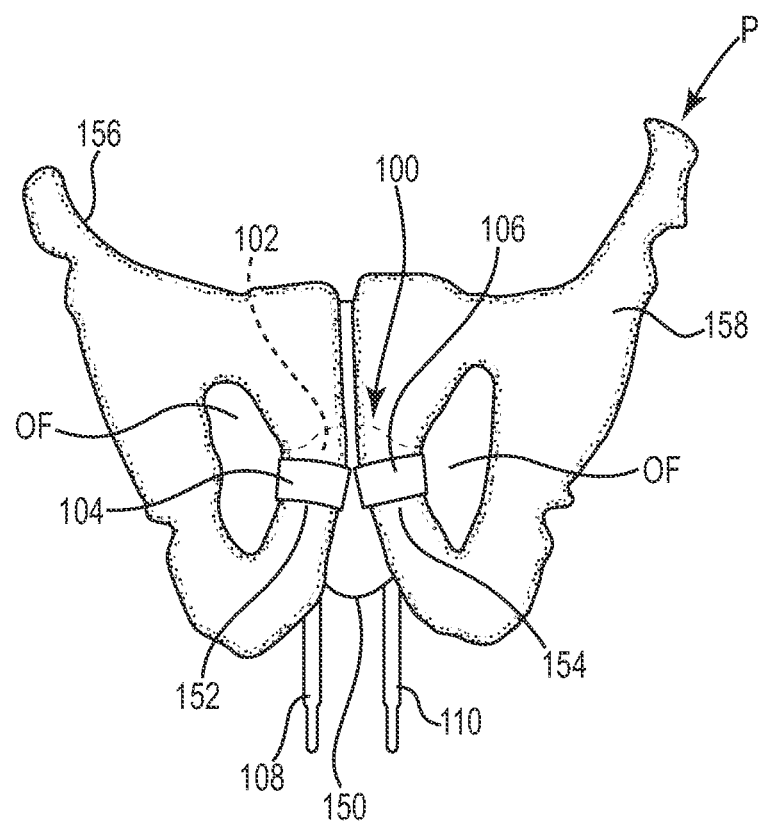
FIG. 7 is a front perspective view of a pelvis including the body implantable device illustrated in FIG. 5.

FIG. 7 is a front perspective view of a pelvis P including the body implantable support 100. The support 100 is provided as a four-arm sub-urethral sling configured to support tissue surrounding a male urethra and relieve incontinence in the male user. In one embodiment, the support 100 is fabricated from the closed loop knit material 60 and has a thickness of between 0.018-0.028 inches, a basis weight of between 85-115 grains per square meter, and a pore size of between 0.35-0.80 square millimeters.

The support 100 is operatively positioned at or distal to the urethral region 150. The trans obturator arm 104 extends through a first one of the obturator foramen OF and the opposing trans obturator arm 106 extends through the opposing obturator foramen OF. The trans obturator arms 104, 106 are coupled to a respective one of the descending rami 152, 154 of the hipbones 156, 158, respectively. The suprapubic arms 108, 110 are shown in a "down" position prior to being implanted into tissue above the location where the arms 104, 106 are attached to the descending rami 152, 154.

The support 1130 is implanted, for example, with the patient in a lithotomy. A vertical perineal incision is made in the midline dissecting to expose the tissue around the urethra near the descending pubic rami 152, 154 bilaterally. The bulbar spongiosis is left intact. A suprapubic transverse incision is made approximately 1 cm proximal and 3 cm lateral to the midline on either side. A suitable introducer (not shown) is inserted from the transverse incision and tunneled either superficially anterior to the pubic symphysis or retropubically to exit through the initial perineal incision. A respective one of the pubic arms 108, 110 is attached to the introducer and pulled through the suprapubic incision. The same maneuver is repeated with the other of the arm 108, 110. In one embodiment, the arms 108, 110 are inserted through the perineal incision by attaching them to the introducer and tunneling the introducer and the arms 108, 110 either superficially anterior to the pubic symphysis or retropubically to exit through the suprapubic incisions. In one embodiment, the introducer is employed to create the exit opening in the abdomen through which the arms 108, 110 are then guided suprapubically.

Figure 8:
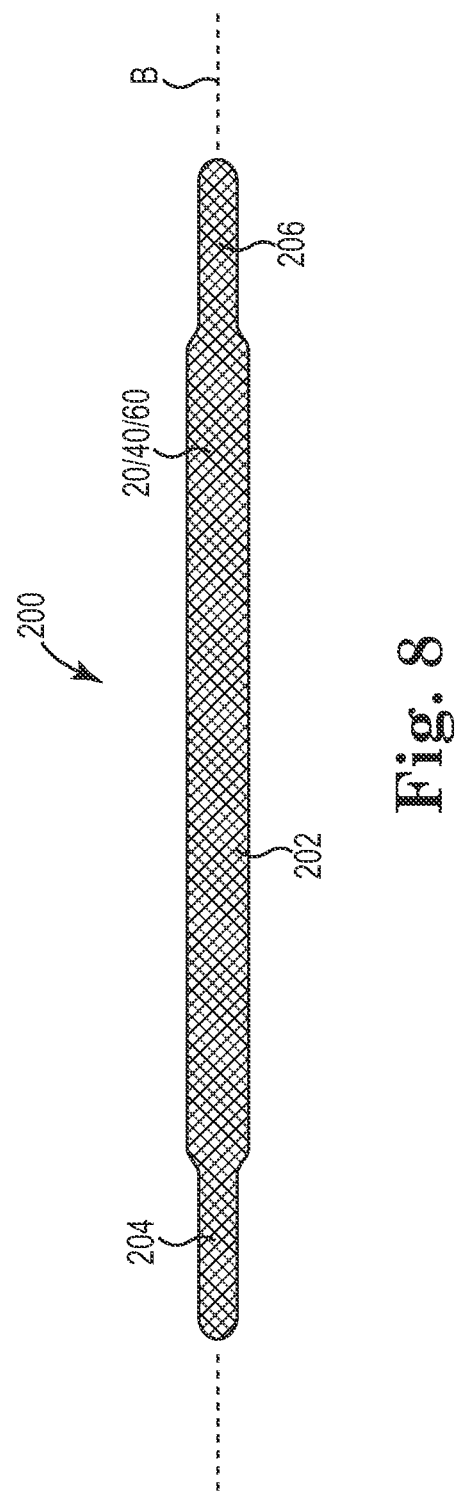
FIG. 8 is a top view of one embodiment of a body implantable device fabricated from a closed loop knit mesh and having two opposed arms.

FIG. 8 is a top view of one embodiment of a body implantable device 200 fabricated from the closed loop knit mesh 20, 40, or 60 and has two opposed arms. In one embodiment, the support 200 is die-cut from one of the closed loop knit meshes 20, 40, or 60 and is employed to treat incontinence in a female patient.

In one embodiment, the device 200 is provided as an incontinence treatment tape configured to support tissue surrounding a female urethra and includes a body 202 with one pair of transobturator arms 204, 206, with each arm 204, 206 extending from an opposed side of the body 202 and oriented on a major axis B. The device 200 is configured to provide a lifting suspension to the female urethra without unduly applying tension to the relatively short (~2 cm) urethra of the female. The closed loop knit mesh of the device 200 has improved tear resistance over known knit mesh female incontinence tapes, which allows the surgeon to implant and manipulate the device 200 with a reduced or eliminated chance of tearing one or both of the trans obturator arms.

In one embodiment, the body implantable device 200 has a length of approximately 60 cm and a width of approximately 2.5 cm. The device 200 is implanted in a minimally invasive surgery by forming midline para-urethral vaginal incision to the region of the middle third of the urethra. The surgeon inserts a finger or other suitable instrument into the vaginal incision to identify the obturator foramen. The surgeon forms a separate skin incision opposite the location so identified relative to the obturator foramen, for example in the groin, to provide an opening through which a needle is passed through the obturator foramen and outward exterior to the body.

In one approach, a needle (not shown) is introduced into this skin incision perpendicular to the perineum for about 15 mm, passing through the internal obturator muscle outside the ischiopubic branch, and is guided by the finger of the surgeon opposite the obturator foramen to the vaginal incision. The end of one of the arms 204, 206 is engaged with the needle that now projects from the vaginal incision. The needle is retracted back through its path to place the arm 204 or 206 through the obturator foramen. Thereafter, the body 202 of the device 200 is placed between the Alban fascia and the periurethral fascia. A similar maneuver is conducted on the opposing side of the patient for the opposite arm 204 or 206. When the tape device 200 is so positioned, the surgeon appropriately tensions the body 202 of the tape device 200 to suspend and support the urethra.

The excess portion of the tape device 200 exterior the body is cut off flush with the skin and the skin incision is suitably immobilized.

Figure 9:
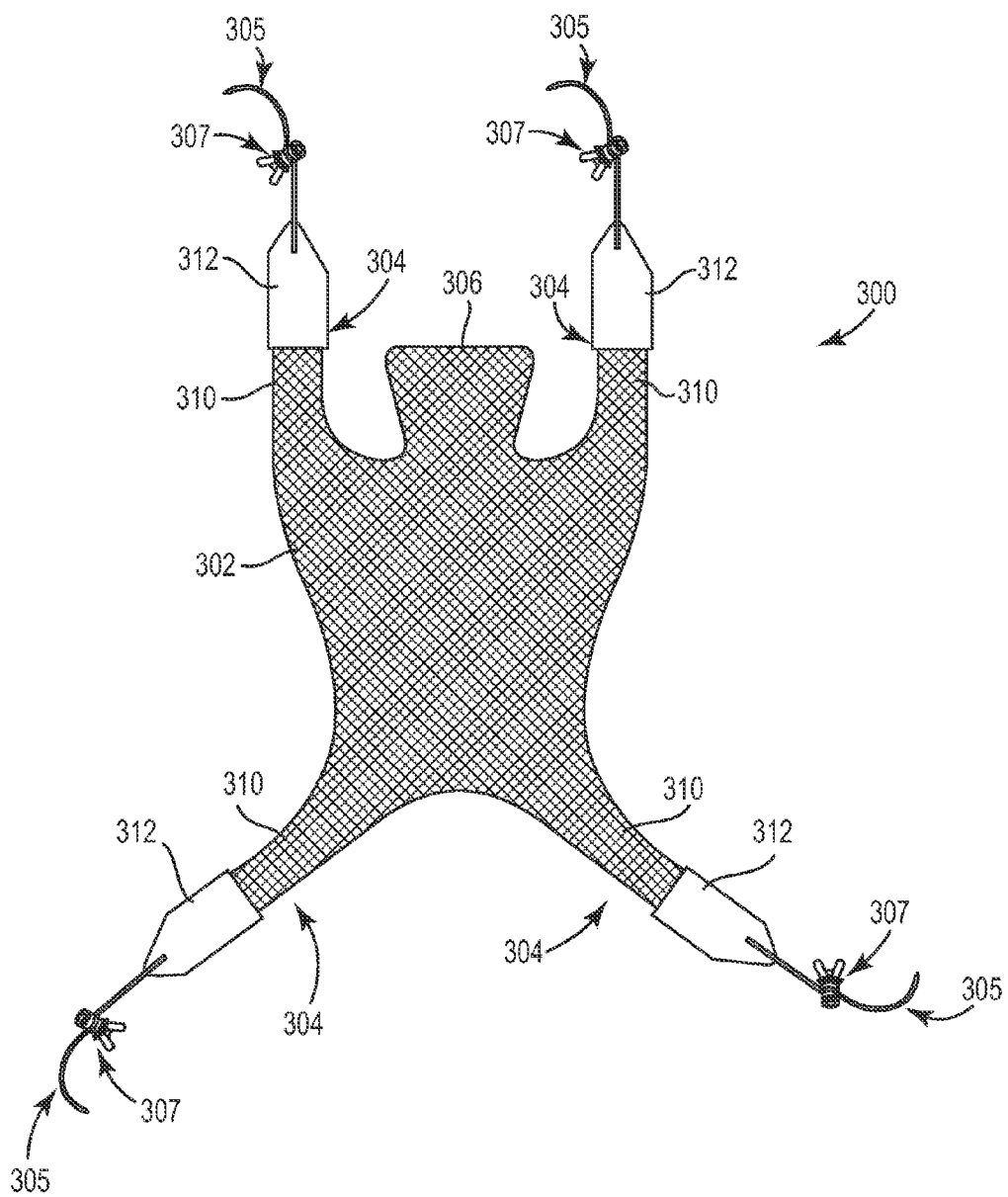
FIG. 9 is a top view of one embodiment of a body implantable device fabricated from a closed loop knit mesh and having multiple arms.

FIG. 9 is a top view of one embodiment of a body implantable device 300 fabricated from one of the closed loop knit meshes 20/40/60 to include multiple arms. In one embodiment, the device 300 is die-cut from one of the closed loop knit meshes 20, 40, or 60 and is employed to repair a pelvic floor in a female patient. In one embodiment, the implantable device 300 is configured to relieve pelvic organ prolapse in women when implanted and includes a support body 302 with at least three arms 304 extending from the support body 302, an interconnecting member 305 that is coupled to each of the arms 304, and an adjustable anchor 307 slidably coupled to each of at least two of the interconnecting members 305.

The adjustable anchors 307 are configured for bi-directional movement along the interconnecting member 305 and exert a compressive force generating frictional interference between the adjustable anchor 307 and the interconnecting member 305. The frictional interference between the adjustable anchor 307 and the interconnecting member 305 inhibits the bi-directional movement of the adjustable anchor 307 along the interconnecting member 305 unless sufficient force is applied to overcome the frictional interference.

The arms 304 in combination with the interconnecting members 305 and the adjustable anchors 307 allow the device 300 to be implanted in a body and adjusted into a desired and tensioned position. The interconnecting members 305 and the adjustable anchors 307 obviate the use of multiple skin exit punctures, and eliminate the use of retriever components and sleeves around the arms 304 that are at times employed when implanting support bodies having arms.

The support body 302 is non-rectangular and the device 300 includes four arms 304 extending from the non-rectangular support body 302. In one embodiment, the support body 302 has a curved outside perimeter with bilateral symmetry relative to a central longitudinal axis of the non-rectangular support body 302. In one embodiment, the support body 302 has four arms 304 and includes a central tail 306 located between two of the arms 304. The central tail 306 is configured for attachment to a suitable pelvic landmark, such as a ligament or other tissue. In one embodiment, the support body 302 is fabricated from a porous closed loop knit mesh 20/40/60 as described herein and is compatible with biological in-situ tissue ingrowth after implantation.

In one embodiment, the arms 304 include a first arm segment 310 extending from support body 302 and a second arm segment 312 extending from the first arm segment 310, where the interconnecting members 305 extend from the second arm segment 312.

In one embodiment, the first arm segments 310 extend 1 cm or more from the support body 302. In one embodiment, one or more of the first arm segments 310 is provided as a "stubby" arm segment that extends from the support body 302 by less than 1 cm, for example. The second arm segment 312 extends from the first arm segment 310 (whether of the "stubby" format or not). The interconnecting member 305 is attached to the second arm segment 312 and one or the other of the adjustable anchor 307 or a fixed anchor (not shown) is attached to the interconnecting member 305.

In one embodiment, an interconnecting member 305 is attached to each arm 304 and an adjustable anchor 307 is attached to each interconnecting member 305. In one embodiment, an interconnecting member 305 is attached to each arm 304 and a fixed anchor is attached to at least one of the interconnecting members 305. It will be recognized that the implantable anatomical device 300 could include one or more adjustable anchors 307 with anywhere from zero to one or more fixed anchors. It is to be appreciated, then, that the device 300 could employ any number of adjustable anchors 307, with or without any number of fixed anchors.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of medical devices as discussed herein. Therefore, it is intended that this invention be limited only by the claims and the equivalents thereof.

What is claimed is:

1. A body implantable fabric comprising:
an organ support device formed from a knit material and comprising a first filament knitted into a first chain of loops that are coupled together by having each loop of the first chain of loops suspended by a neighboring loop of the knit material, the filament being tied around individual loops along the first wale to form a plurality of closed loops that configure the organ support device to have a tear resistance of not less than 5 lbf, each of the closed loops including the filament defining an ascending loop segment, a first descending loop segment, a transverse loop segment, and a second descending loop segment, the ascending loop segment passing upwardly from a descending loop segment of a first neighboring loop in the first wale and then curving downwardly to transition to the first descending loop segment, the first descending loop segment then extending downwardly to transition to a transverse loop segment that is tied transversely around the ascending loop segment of the filament, the transverse loop segment then curving downwardly to transition to the second descending loop segment, the second descending loop segment then transitioning into an ascending loop segment of a second neighboring loop in the first wale and positioned opposite the first neighboring loop in the first wale.

2. The body implantable fabric of claim 1, wherein the knit material comprises a second filament different than the first filament that forms a second chain of loops, the first chain of loops coupled with the second chain of loops.

3. The body implantable fabric of claim 1, wherein the organ support device includes a body portion and an arm extending from the body portion, the arm having a tear resistance of not less than 5 lbf.

4. The body implantable fabric of claim 1, wherein the organ support device is separated from a larger sheet of the knit material and includes a body portion and at least one pair of arms.

5. The body implantable fabric of claim 4, wherein the organ support device includes a first pair of linearly opposed arms and a second pair of parallel arms, the parallel arms perpendicular to the linearly opposed arms.

6. The body implantable fabric of claim 4, wherein the organ support device is a male urethra support device including a first pair of linearly opposed obturator arms and a pair of substantially parallel suprapubic arms.

7. The body implantable fabric of claim 4, wherein the organ support device is a female urethra support tape having one pair of transobturator arms.

8. The body implantable fabric of claim 4, wherein the organ support device is a female pelvic organ support device including a plurality of arms extending from a body.

9. The body implantable fabric of claim 1, wherein the knit material has a thickness of between 0.018-0.028 inches, a basis weight of between 85-115 grams per square meter, and a pore size of between 0.35-0.80 square millimeters.

10. The body implantable fabric of claim 1, wherein the chain of loops extend along an arm of the organ support device.

11. The body implantable fabric of claim 10, wherein the arm of the support is a transobturator arm sized for passage through an obturator foramen of a user, and the at least one closed loop configures the transobturator arm to have a 90 degree tear resistance of more than 5 lbf in accordance with ASTM D2261.

12. A body implantable fabric comprising:
an organ support device formed from a knit material, where the knit material comprises a first filament knitted into a first chain of loops that extend along a first wale, the first filament being tied around individual alternating loops in the first chain of loops along the first wale to form a first chain of closed loops, and a second filament knitted into a second chain of loops that extend along a second wale, the second filament being tied around individual alternating loops in the second chain of loops along the second wale to form a second chain of closed loops, each loop of the first and second chains of loops being suspended by a neighboring loop of the knit material, each of the closed loops of the first chain of loops including the first filament defining an ascending loop segment, a first descending loop segment, a transverse loop segment, and a second descending loop segment, the ascending loop segment passing upwardly from a descending loop segment of a first neighboring loop in the first wale and then curving downwardly to transition to the first descending loop segment, the first descending loop segment then extending downwardly to transition to a transverse loop segment that is tied transversely around the ascending loop segment of the first filament, the transverse loop segment then curving downwardly to transition to the second descending loop segment, the second descending loop segment then transitioning into an ascending loop segment of a second neighboring loop in the first wale and positioned opposite the first neighboring loop in the first wale.

* * * * *